United States Patent
Gim et al.

(10) Patent No.: US 8,688,981 B2
(45) Date of Patent: Apr. 1, 2014

(54) METHOD AND APPARATUS FOR LOGGING IN A HEALTH INFORMATION TELE-MONITORING DEVICE BY USING A PERSONAL PORTABLE DEVICE

(75) Inventors: Byung-soo Gim, Yongin-si (KR);
Kyu-tae Yoo, Seongnam-si (KR);
Kwang-hyeon Lee, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 330 days.

(21) Appl. No.: 12/553,297

(22) Filed: Sep. 3, 2009

(65) Prior Publication Data

US 2010/0122087 A1 May 13, 2010

(30) Foreign Application Priority Data

Nov. 11, 2008 (KR) .................. 10-2008-0111863

(51) Int. Cl.
*H04L 29/06* (2006.01)
(52) U.S. Cl.
USPC ........... 713/168; 713/169; 713/170; 713/171; 713/172; 726/27; 726/28; 726/29; 726/30
(58) Field of Classification Search
USPC .................. 380/277; 713/168, 183, 184, 202; 726/7, 10; 396/56; 600/300
See application file for complete search history.

(56) References Cited

U.S. PATENT DOCUMENTS

| | | | | |
|---|---|---|---|---|
| 6,443,890 B1 * | 9/2002 | Schulze et al. | ................ | 600/300 |
| 7,603,029 B2 * | 10/2009 | Suh et al. | ................ | 396/56 |
| 7,826,619 B2 * | 11/2010 | Hanaoka | ................ | 380/277 |
| 2003/0166994 A1 | 9/2003 | Ooshima et al. | | |
| 2004/0133812 A1 * | 7/2004 | Ohmori et al. | ................ | 713/202 |
| 2007/0079135 A1 * | 4/2007 | Saito | ................ | 713/183 |
| 2007/0213856 A1 | 9/2007 | Kosaka | | |
| 2008/0101597 A1 * | 5/2008 | Nolan et al. | ................ | 380/30 |
| 2009/0025072 A1 * | 1/2009 | Kondo | ................ | 726/7 |
| 2009/0222458 A1 * | 9/2009 | Hattori | ................ | 707/10 |

FOREIGN PATENT DOCUMENTS

| | | |
|---|---|---|
| JP | 2002-366665 A | 12/2002 |
| JP | 2002360580 A | 12/2002 |
| JP | 2005-182317 A | 7/2005 |
| JP | 2005-216210 A | 8/2005 |
| JP | 2006-195669 A | 7/2006 |
| JP | 2007-188363 A | 7/2007 |
| KR | 1020060067260 A | 6/2006 |
| KR | 1020080023712 A | 3/2008 |
| KR | 1020080027541 A | 3/2008 |
| KR | 1020080052088 A | 6/2008 |
| KR | 1020080060543 A | 7/2008 |
| WO | 03/005891 A1 | 1/2003 |

* cited by examiner

*Primary Examiner* — Longbit Chai
(74) *Attorney, Agent, or Firm* — Cantor Colburn LLP

(57) ABSTRACT

A method of logging in a health information tele-monitoring device by using a personal portable device. The method includes issuing a security key embedded in a health information tele-monitoring device to a personal portable device, storing the security key issued by the health information tele-monitoring device in the user's personal portable device; requesting the user's personal portable device to authenticate the health information tele-monitoring device in order to connect the health information tele-monitoring device to a healthcare server; and authorizing access of the health information tele-monitoring device to the healthcare server.

7 Claims, 3 Drawing Sheets

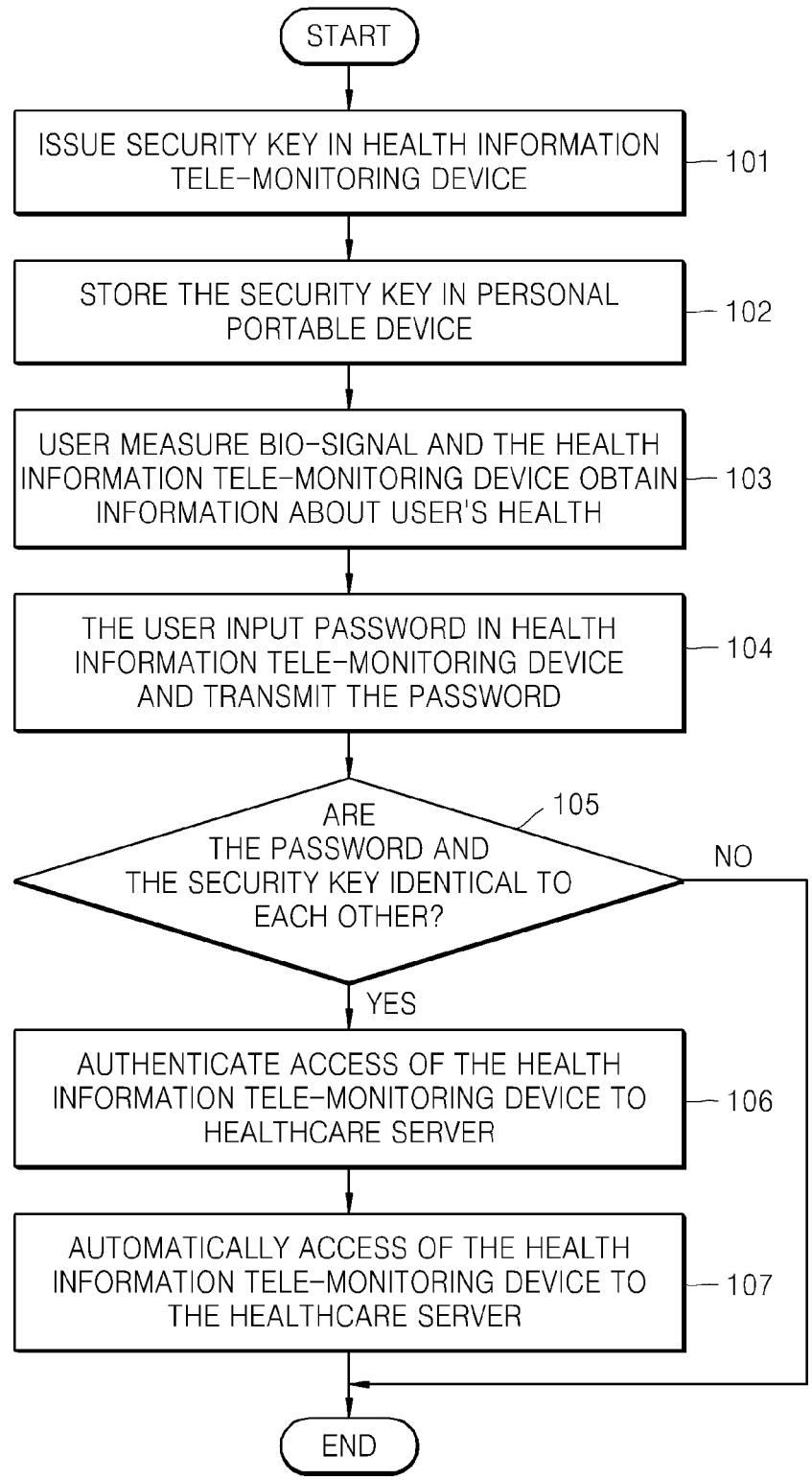

METHOD AND APPARATUS FOR LOGGING IN A HEALTH INFORMATION TELE-MONITORING DEVICE BY USING A PERSONAL PORTABLE DEVICE

CROSS-REFERENCE TO RELATED APPLICATIONS

This application claims the priority to Korean Patent Application No. 10-2008-0111863, filed on Nov. 11, 2008, and all the benefits accruing therefrom under 35 U.S.C. §119, the content of which in its entirety is herein incorporated by reference.

BACKGROUND

1. Field

One or more embodiments relate to a method and apparatus for logging in a health information tele-monitoring device by using a personal portable device.

2. Description of the Related Art

Research into remote medical systems and remote health monitoring has been conducted to remotely provide users with medical information and service. It is desirable to securely transmit information about users' health in order to provide remote medical information and service. In the U.S., the Health Insurance Portability and Accountability Act ("HIPAA") was enacted to address the security and privacy of health data. Public key cryptography and secret key cryptography are used for secure communication as cryptographic methods. These cryptographic methods enable the issue of initial encryption keys on the Internet.

SUMMARY

One or more embodiments include a method and apparatus for logging in a health information tele-monitoring device by using a personal portable device in order to securely communicate information about a users' health.

Additional aspects, features and advantages will be set forth in part in the description which follows.

To achieve the above and/or other aspects, features or advantages, one or more embodiments includes a method of logging in a health information tele-monitoring device by using a user's personal portable device. The method includes: issuing a security key embedded in a health information tele-monitoring device to a user's personal portable device; storing the security key issued by the health information tele-monitoring device in the user's personal portable device; requesting the user's personal portable device to authenticate the health information tele-monitoring device in order to connect the health information tele-monitoring device to a healthcare server; and authorizing access of the health information tele-monitoring device to the healthcare server.

To achieve the above and/or other aspects, features or advantages, one or more embodiments includes a health information tele-monitoring device including: a health information obtaining unit which obtains information about a user's health; a security key issuing unit which issues a security key; a local communicating unit which transmits the security key to a personal portable device through a local communication; and a network communicating unit which transmits the information about the user's health to a healthcare server over a network or transmits information from the healthcare server to a user over the network.

To achieve the above and/or other aspects, features or advantages, one or more embodiments includes a personal portable device including: a security key obtaining unit which obtains a security key transmitted from a health information tele-monitoring device; a security key storage unit which stores the security key; a comparing unit which compares the security key with a password of the health information tele-monitoring device and transmits a signal informing that the health information tele-monitoring device is authorized to access the healthcare server if the comparing unit determines that the security key and the password are identical to each other.

BRIEF DESCRIPTION OF THE DRAWINGS

These and/or other aspects, advantages and features of this disclosure will become apparent and more readily appreciated from the following further description of the embodiments, taken in conjunction with the accompanying drawings in which:

FIG. 3 is a flowchart illustrating an exemplary embodiment of a method of logging in the health information tele-monitoring device, an exemplary embodiment of which is shown in FIG. 1.

DETAILED DESCRIPTION

Figure 1:
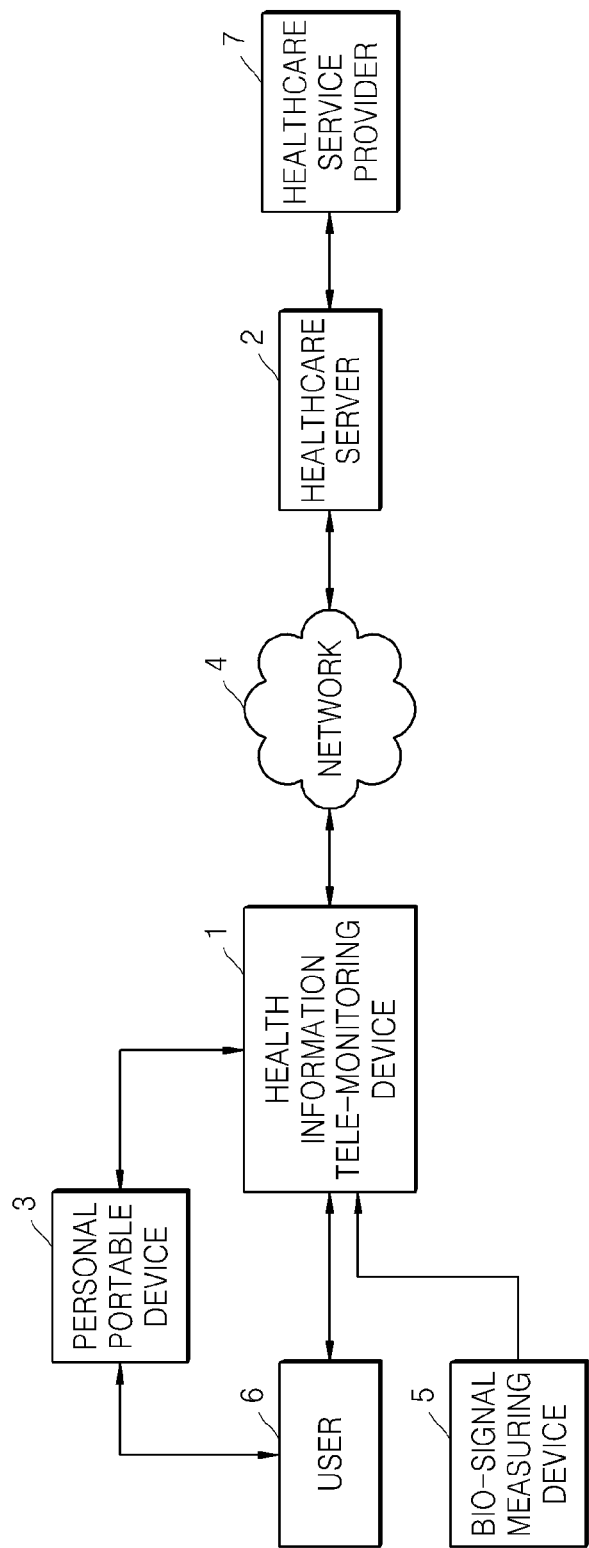
FIG. 1 is a flowchart illustrating an exemplary embodiment of an environment for secure communication of personal health information.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to further explain aspects, advantages and features of the present description.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising,"

or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to other elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The embodiments described herein should not be construed as limited to the particular shapes of regions as illustrated herein but are to include deviations in shapes. Thus, the regions illustrated in the figures are schematic in nature and their shapes are not intended to limit the scope of the present claims.

FIG. 1 is a flowchart illustrating an exemplary embodiment of an environment for secure communication of personal health information. Referring to FIG. 1, the environment for secure communication of personal health information includes a health information tele-monitoring device 1, a healthcare server 2, a personal portable device 3, a network 4, a bio-signal measuring device 5, a user 6, and a healthcare service provider 7.

The user 6 measures a health condition of the user 6 by using the bio-signal measuring device 5. The health information tele-monitoring device 1 obtains information regarding the health condition of the user 6 from the bio-signal measuring device 5. The health information tele-monitoring device 1 and the personal portable device 3 wirelessly perform one-to-one local communication. The health information tele-monitoring device 1 and the healthcare server 2 communicate each other over the network 4. The healthcare service provider 7 obtains the information regarding the health condition of the user 6 through the healthcare server 2.

Hereinafter, although the health information tele-monitoring device 1 and the bio-signal measuring device 5 are separated from each other, it will be understood by those of ordinary skill in the art that the health information tele-monitoring device 1 and the bio-signal measuring device 5 may be united into a single device. For example, a function of the health information tele-monitoring device 1 may be embedded in the bio-signal measuring device 5.

Figure 2:
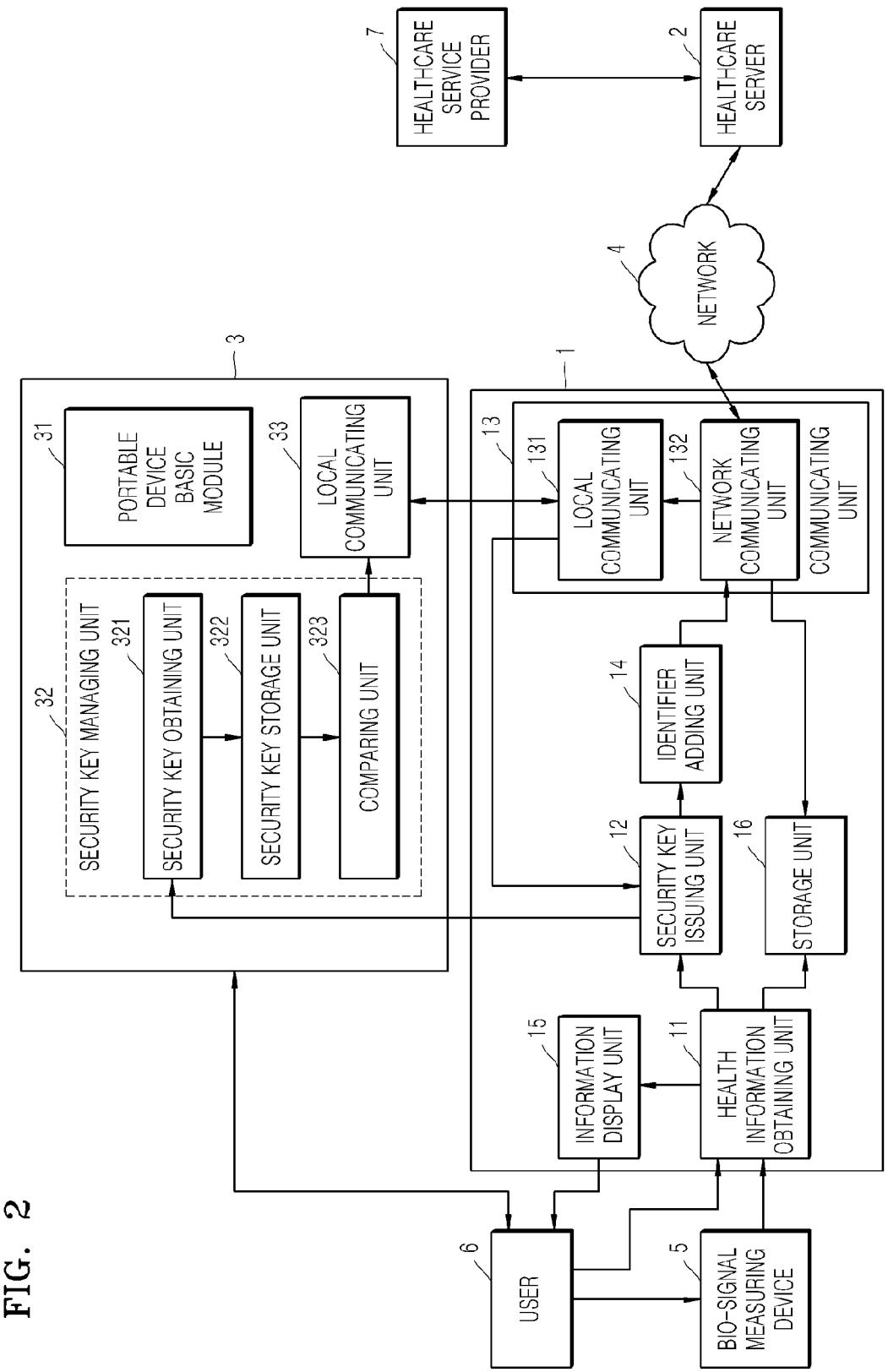
FIG. 2 is a block diagram showing an exemplary embodiment of a health information tele-monitoring device, an exemplary embodiment of which is shown in FIG. 1, and a personal portable device, an exemplary embodiment of which is also shown in FIG. 1.

FIG. 2 is a block diagram showing an exemplary embodiment of the health information tele-monitoring device 1 and the personal portable device 3.

Referring to FIG. 2, the bio-signal measuring device 5 is a medical device and equipment for measuring a bio-signal of the user 6. For example, the bio-signal measuring device 5 includes an electroencephalograph, an electroencephalogram analyzer, a retinal electrometer, a sphygmograph, a fetal monitor, a thermography, a hemopiezometer, a slit lamp microscope, an extensometer, a phonocardiograph, an electrocardiograph, a thermometer, a body weight scale, an ultrasonic blood flow meter, a hemopiezometer, a spirometer, or the like or a combination thereof. In this regard, a bio-signal includes an electroencephalogram analysis material, an electromyogram, a temperature, a body weight, an obesity index, a body mass index, a liver value, a cholesterol value, a blood sugar level, or the like or a combination thereof.

It will be understood by those of ordinary skill in the art that the bio-signal may include a health-related value, condition, or symptom, and the bio-signal measuring device 5 may include a device or equipment for obtaining the bio-signal.

The health information tele-monitoring device 1 may include a health information obtaining unit 11, a security key issuing unit 12, a communicating unit 13, an identifier adding unit 14, an information display unit 15, a storage unit 16, or the like or a combination thereof.

The health information obtaining unit 11 obtains information regarding the condition of the user 6 from the bio-signal measuring device 5. In this regard, the user 6 inputs the information regarding the health condition of the user 6 into the health information obtaining unit 11, or the bio-signal measuring device 5 connected to the health information tele-monitoring device 1 directly inputs the information regarding the health condition of the user 6 into the health information obtaining unit 11. The user 6 or the healthcare service provider 7 selects how the health information obtaining unit 11 obtains the information regarding the health condition of the user 6. For example, if the bio-signal measuring device 5 is the thermometer, the health information obtaining unit 11 obtains information regarding the temperature of the user 6 measured by the thermometer. In this regard, the user 6 may input data of the temperature of the user 6 measured by the thermometer into the health information obtaining unit 11, or the health information obtaining unit 11 may directly receive the data of the temperature of the user 6 from the thermometer. The health information obtaining unit 11 corresponding to a user terminal may be designed to be connected to the bio-signal measuring device 5 or include a function of the bio-signal measuring device 5.

The security key issuing unit 12 issues a security key embedded in the health information tele-monitoring device 1 to the personal portable device 3.

The communicating unit 13 includes a first local communicating unit 131 and a network communicating unit 132. The first local communicating unit 131 transmits the security key issued by the health information tele-monitoring device 1 to a security key obtaining unit 321 included in the personal portable device 3 through a local communication. If the user 6 inputs a password into the health information tele-monitoring device 1 in order to transmit the bio-signal to the healthcare server 2, the first local communicating unit 131 transmits the password to a comparing unit 323 included in the personal portable device 3. The network communicating unit 132 transmits information about the user 6 that includes an identifier of the user terminal added by the identifier adding unit 14 to the healthcare server 2 over the network 4 or receives information from the healthcare server 2 over the network 4.

Although the network 4 may, in an embodiment, be the Internet, it will be understood by one of ordinary skill in the art that a different type of network, such as a wireless local area network ("LAN"), or the like, for example, but is not limited thereto, may be used as the network.

The identifier adding unit 14 adds the identifier of the user terminal, i.e., the health information tele-monitoring device 1, to information output by the security key issuing unit 12. The identifier of the health information tele-monitoring device 1 refers to a symbol or a collection of symbols used to exhibit the characteristics of the health information tele-monitoring device 1. The healthcare server 2 identifies the health information tele-monitoring device 1 among a plurality of health information tele-monitoring devices, which communicate with the healthcare server 2 based on the identifier of the health information tele-monitoring device 1.

The information display unit 15 displays a result obtained by measuring the bio-signal of the user 6 and information received from the healthcare server 2. The information display unit 15 includes a device (e.g., a display, a liquid crystal display ("LCD") screen, a light emitting display ("LED"), a scale display device or the like) for displaying visual information, a device (e.g., a speaker or the like) for transmitting auditory information, or the like.

The storage unit 16 stores the result obtained by measuring the bio-signal of the user 6 and the information received from the healthcare server 2. The user 6 selects whether to store the result obtained by measuring the bio-signal of the user 6 and the information received from the healthcare server 2 in the storage unit 16. That is, the user 6 controls the health information tele-monitoring device 1 to store desired information.

The personal portable device 3 includes a portable device basic module 31, a security key managing unit 32 and a second local communicating unit 33. The portable device basic module 31 is a basic module for performing a basic function of a general personal portable device.

The security key managing unit 32 includes the security key obtaining unit 321, a security key storage unit 322 and the comparing unit 323.

The security key obtaining unit 321 obtains the security key issued by the health information tele-monitoring device 1. The security key storage unit 322 stores the security key. The comparing unit 323 compares the password input by the user 6 with the security key and determines whether the password and the security key are identical to each other.

When the comparing unit 323 determines that the password and the security key are identical to each other, the second local communicating unit 33 transmits a signal informing that the health information tele-monitoring device 1 is authorized to access the healthcare server 2, to the health information tele-monitoring device 1.

If the user 6 inputs a password into the health information tele-monitoring device 1 and requests the personal portable device 3 to authenticate the health information tele-monitoring device 1 so as to attempt access of the health information tele-monitoring device 1 to the healthcare server 2, i.e., if the user 6 requests an authentication of access to the healthcare server 2, the second local communicating unit 33 compares a previously stored security key with the password. If the password and the previously stored security key are identical to each other, the personal portable device 3 automatically authorizes access of the health information tele-monitoring device 1 to the healthcare server 2. Thereafter, the health information tele-monitoring device 1 is automatically accessed to the healthcare server 2 so that the health information tele-monitoring device 1 and the healthcare server 2 share the information regarding the condition of the user 6. In more detail, the health information tele-monitoring device 1 transmits the information about the user 6, which includes the identifier of the health information tele-monitoring device 1 added by the identifier adding unit 14, to the healthcare server 2 over the network 4 or receives the information of the healthcare server 2 over the network 4.

Therefore, input of the password into the health information tele-monitoring device 1 makes it possible to reinforce the security of health information by using the personal portable device 3.

FIG. 3 is a flowchart illustrating an exemplary embodiment of a method of logging in the health information tele-monitoring device 1, an exemplary embodiment of which is shown in FIG. 1. Referring to FIG. 3, the method of logging in the health information tele-monitoring device 1 of an embodiment comprises operations sequentially processed by the health information tele-monitoring device 1 and the personal portable device 3 shown in FIG. 1. Therefore the foregoing disclosure will not be repeated and the description with regard to the health information tele-monitoring device 1 and the personal portable device 3 is applicable to an embodiment of the method of logging in the health information tele-monitoring device 1.

In first operation 101, the health information tele-monitoring device 1 issues a security key embedded in the health information tele-monitoring device 1 to the personal portable device 3 through local communication.

In second operation 102, the personal portable device 3 obtains and stores the security key issued by the health information tele-monitoring device 1.

In third operation 103, if the user 6 measures the health condition of the user 6 by using the bio-signal measuring device 5, the health information tele-monitoring device 1 obtains information regarding the health condition of the user 6 from the bio-signal measuring device 5.

In fourth operation 104, if the user 6 inputs a password into the health information tele-monitoring device 1 in order to transmit a bio-signal of the user 6 to the healthcare server 2, the health information tele-monitoring device 1 transmits the password to the personal portable device 3 through local communication and requests the personal portable device 3 to authenticate the health information tele-monitoring device 1.

In fifth operation 105, the personal portable device 3 compares the password input by the user 6 with the security key and determines whether the password and the security key are identical to each other. If the personal portable device 3 determines that the password and the security key are identical to each other, the personal portable device 3 proceeds to sixth operation 106, and if the personal portable device 3 determines that the password and the security key are not identical to each other, the personal portable device 3 does not proceed to another operation.

In sixth operation 106, the personal portable device 3 authenticates access of the health information tele-monitoring device 1 to the healthcare server 2.

In seventh operation 107, the health information tele-monitoring device 1 automatically has access to the healthcare server 2 so that the health information tele-monitoring device and the healthcare server 2 share the information regarding the condition of the user 6.

As described above, according to one or more of the above embodiments, when information regarding user's condition is transmitted to a designated healthcare server or the healthcare server is connected to a health information tele-monitoring device to obtain the information regarding user's condition, before a user logs in the health information tele-monitoring device to allow a connection of the health information tele-monitoring device to the healthcare server, the health information tele-monitoring device connected to a user's personal portable device authenticates the user by using a security key embedded in the user's personal portable device, and the user's personal portable device authenticates access of the health information tele-monitoring device to the healthcare server, thereby providing the reinforced security of the information about user's condition.

It should be understood that the exemplary embodiments described herein should be considered in a descriptive sense only and not for purposes of limitation. Descriptions of features, advantages or aspects within each embodiment should be considered as available for other features, advantages or aspects in other embodiments.

What is claimed is:

1. A method of logging in a health information tele-monitoring device by using a user's personal portable device, the method comprising:

issuing a security key embedded in a health information tele-monitoring device;

transmitting the issued security key to the user's personal portable device to allow the security key to be stored in the user's personal portable device before a user attempts to log in the health information tele-monitoring device;

measuring a health condition of the user with a bio-signal measuring device;

transmitting a password, input by the user into the health information tele-monitoring device, to the user's personal portable device to request the user's personal portable device to authenticate the health information telemonitoring device in order to connect the health information tele-monitoring device to a healthcare server; and receiving a signal, from the user's personal portable device, informing that the health information tele-monitoring device is authorized to access the healthcare server for information of the user health condition, wherein the signal is generated by the user's personal portable device if the security key stored in the user's personal portable device and the password transmitted from the health information tele-monitoring device are identical to each other.

2. The method of claim 1, wherein the health information tele-monitoring device and the user's personal portable device wirelessly communicate with each other.

3. The method of claim 1, wherein the health information tele-monitoring device and the user's personal portable device perform one-to-one local communication.

4. The method of claim 1, further comprising sharing information about user's health between the health information tele-monitoring device and the healthcare server, wherein after the authentication, the health information tele-monitoring device automatically has access to the healthcare server.

5. A health information tele-monitoring device, comprising:

a health information obtaining unit which obtains information from a bio-signal measuring unit about a user's health;

a security key issuing unit which issues a security key;

a local communicating unit which transmits the security key to a personal portable device through a local communication, the security key to be stored in the user's personal portable device before a user attempts to log in the health information tele-monitoring device; and a network communicating unit which transmits the information about the user's health to a healthcare server over a network or transmits healthcare information from the healthcare server to the user over the network, wherein the transmission of the information about the user's health to the healthcare server over the network or the transmission of the healthcare information from the healthcare server to the user over the network occurs if the personal portable device authenticates the health information tele-monitoring device to connect to the healthcare server, wherein the authentication includes comparing the security key transmitted to and stored in the user's personal portable device to a password input by the user into the health information tele-monitoring device, determining whether the security key transmitted to and stored in the user's personal portable device and the password input by the user are identical to each other and authorizing access of the health information tele-monitoring device to the healthcare server if the security key stored in the user's personal portable device and the password input by the user are identical to each other.

6. The device of claim 5, further comprising an identifier adding unit which adds an identifier of the health information tele-monitoring device to the information about the user's health, wherein the network communicating unit transmits the information about the user's health, including the identifier, to the healthcare server.

7. A personal portable device comprising:

a security key obtaining unit which obtains a security key transmitted from a health information tele-monitoring device;

a security key storage unit which stores the security key before a user attempts to log in the health information tele-monitoring device;

a comparing unit which compares the security key with a password input by the user into the health information tele-monitoring device and determines whether the security key and the password are identical to each other; and a transmitting unit which transmits a signal informing that the health information tele-monitoring device is authorized to access the healthcare server for user's health information if the comparing unit determines that the security key and the password are identical to each other.

* * * * *